United States Patent
Perry et al.

[11] Patent Number: 5,865,810
[45] Date of Patent: Feb. 2, 1999

[54] SKIN PROTECTOR FOR ULTRASONIC-ASSISTED LIPOSUCTION AND ACCESSORIES

[76] Inventors: Larry C. Perry, 3333 Country Ridge Dr., Antioch, Tenn. 37013; G. Patrick Maxwell, 4416 Gerald Pl., Nashville, Tenn. 37205

[21] Appl. No.: 848,995

[22] Filed: May 2, 1997

Related U.S. Application Data

[60] Division of Ser. No. 588,615, Jan. 19, 1996, Pat. No. 5,651,773, and a continuation-in-part of Ser. No. 588,615.

[51] Int. Cl.⁶ .................................................. A61M 5/32
[52] U.S. Cl. .............................................. 604/174; 604/93
[58] Field of Search ........................... 604/19, 21, 174, 604/175, 164, 264, 902, 283, 905, 268, 93, 104, 109, 117, 165, 274

[56] References Cited

U.S. PATENT DOCUMENTS

| | | | |
|---|---|---|---|
| 5,213,567 | 5/1993 | Masaki | 604/19 |
| 5,226,890 | 7/1993 | Ianniruberto et al. | 604/164 |
| 5,257,973 | 11/1993 | Villasuso | 604/49 |
| 5,258,003 | 11/1993 | Ciaglia et al. | 606/185 |
| 5,380,334 | 1/1995 | Torrie et al. | 606/104 |
| 5,490,843 | 2/1996 | Hildwein et al. | 604/164 |
| 5,507,744 | 4/1996 | Tay et al. | 606/50 |
| 5,755,697 | 5/1998 | Jones et al. | 604/174 |

*Primary Examiner*—Wynn Wood Coggins
*Assistant Examiner*—Cris L. Rodriguez
*Attorney, Agent, or Firm*—Paul M. Craig, Jr.

[57] ABSTRACT

A skin protector and accessories for protection of a skin incision during minimally invasive surgical procedures requiring protection from thermal and frictional abrasion, for example, during ultrasonic-assisted liposuction. The skin protector incorporates an outer configuration to assist in maintaining in situ positioning of the skin protector during operative procedure. An introducer member for blunt dissection of a tunnel is provided to allow easy insertion of the skin protector. A driver member for dilatation of the skin incision, and for facilitating implantation and withdrawal of the skin protector is provided with a complementary configuration to that of the skin protector to cause the skin protector to be taken along with rotary motion of the driver member.

21 Claims, 5 Drawing Sheets

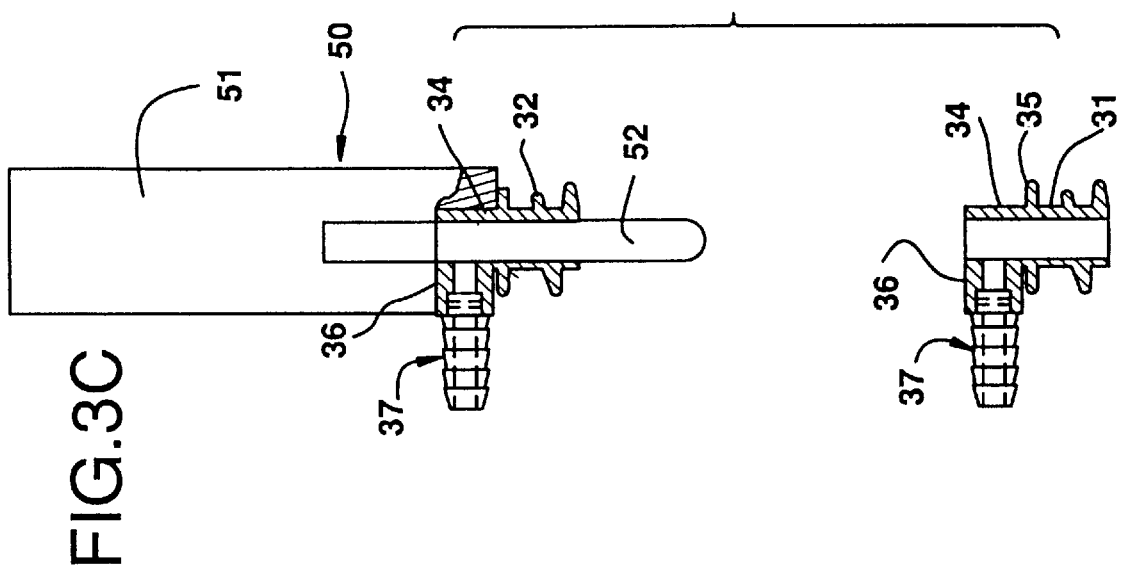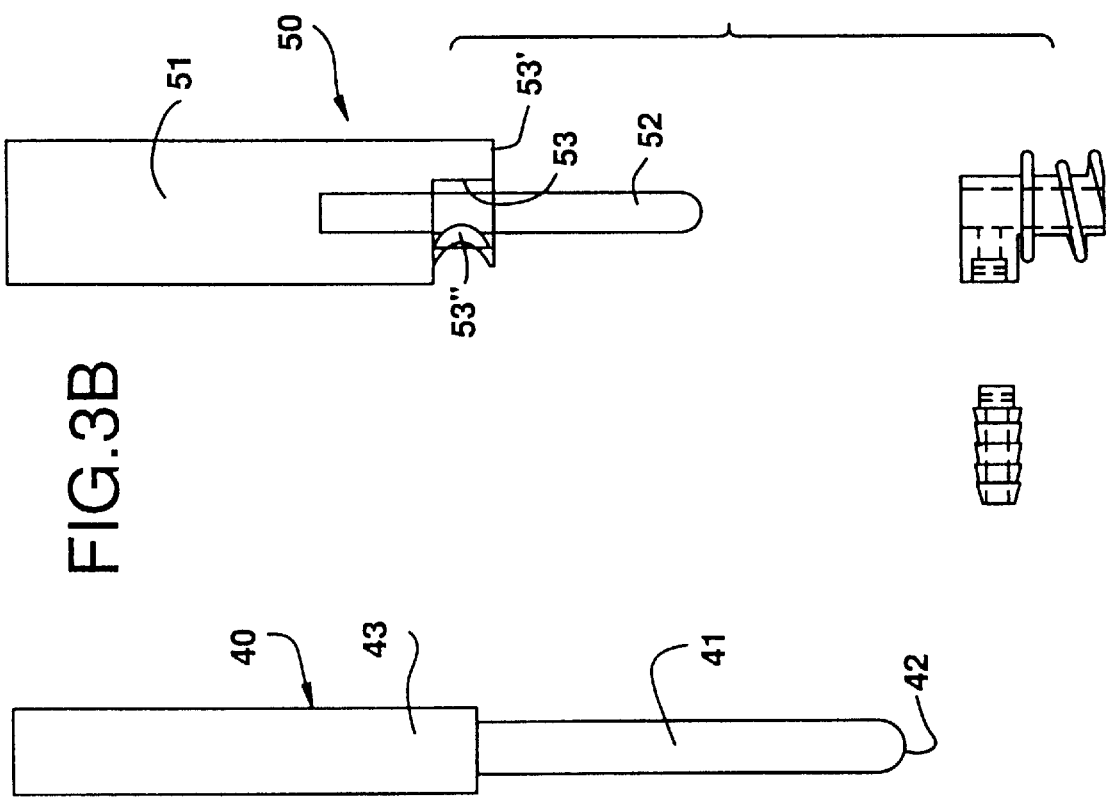

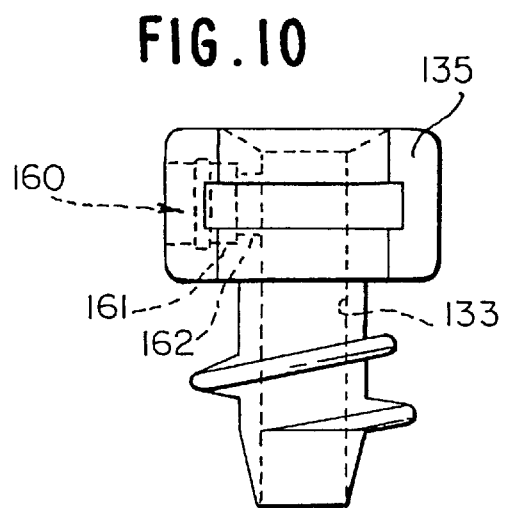
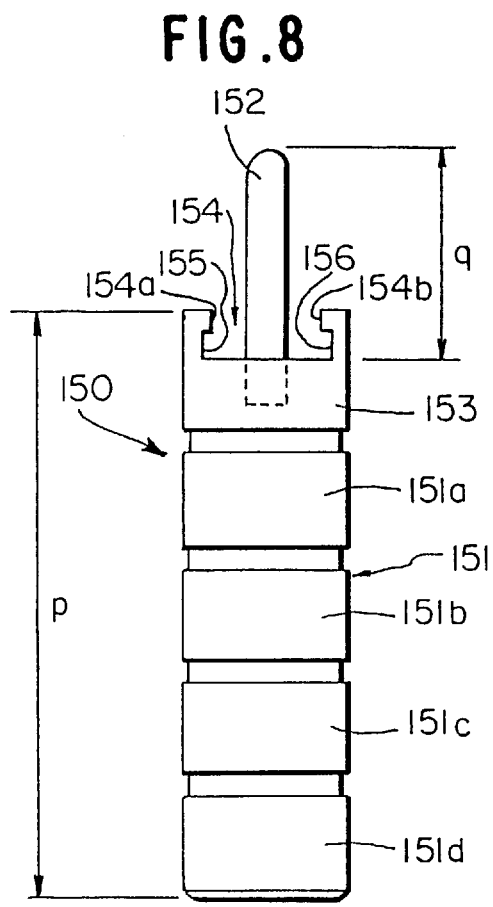
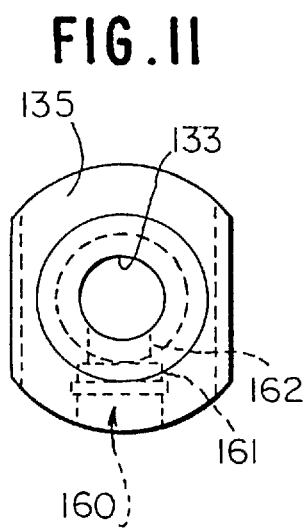
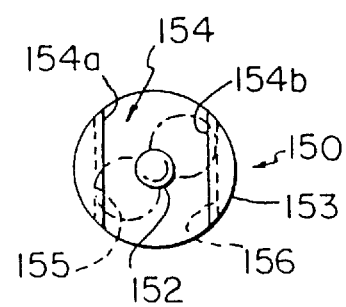

SKIN PROTECTOR FOR ULTRASONIC-ASSISTED LIPOSUCTION AND ACCESSORIES

RELATED CASES

This application is a combined divisional and continuation-in-part application of our application Ser. No. 08/588,615, filed in the United States Patent and Trademark Office on Jan. 19, 1996, U.S. Pat. No. 5,651,773 and entitled "Skin Protector For Ultrasonic-Assisted Liposuction and Accessories."

FIELD OF INVENTION

This invention relates to a skin protector and accessories, especially for use in ultrasonic-assisted liposuction.

BACKGROUND OF THE INVENTION

The surgical treatment of lipodystrophy using suction-assisted lipectomy has evolved rather dramatically over the past fifteen years. It was first introduced in Europe in the late 1970's and began to attract attention in the United States in the early 1980's. It was first practiced using sharp curettage with secondary suction and later evolved to a more controlled vacuum suctioning of fat using large blunt cannulas. Eventually smaller specialized cannulas and various suction techniques were introduced allowing more selective and controlled removal of adipose tissue. More recently, the introduction of the tumescent technique has reduced fluid and electrolyte shifts allowing larger volumes of fat to be removed.

The most recent "advance" in the field of body contouring is the introduction of ultrasonic-assisted liposuction. The application of ultrasonic energy to adipose tissue "emulsifies" the fat by cellular cavitation causing the release of fatty acids into the intercellular spaces. The combination of the free fatty acids, normal interstitial fluid and the tumescent fluid forms a stable fatty emulsion which can then be extracted from the subcutaneous space using small suction cannulas. Proponents of this technique contend that it is a safe method of body contouring and that it has a number of advantages over traditional liposuction techniques. It is reported to allow greater suction volumes per patient with significantly less blood loss, better control of contour and physical alteration of the overlying skin.

The equipment and instrumentation used for ultrasonic-assisted liposuction generally consist of an electrical signal generator, a hand-piece unit including a piezoelectric crystal to transform the electrical energy from the generator into mechanical vibration and a solid or hollow probe which amplifies the longitudinal motion and provides the direct surface area (tip) for generating cellular cavitation. Various probes have been designed in an attempt to facilitate the evacuation of aspirate during the application of ultrasonic energy. In addition, some probes allow for the infusion of fluid within, or around the probe, providing a cooling mechanism for the probe-soft tissue interface.

The surgical procedure requires a full thickness linear skin incision. The ultrasonic probe or cannula is delivered through the skin incision. The probe is continuously placed in motion by the surgeon during the application of ultrasonic energy as research has demonstrated static positioning may potentially increase the risk of thermal abrasion.

SUMMARY OF THE INVENTION

A principal object of the present invention is to provide surgical tools for procedures which require the need for protecting the incisional site from frictional or thermal abrasion as may occur, for example, in minimally invasive surgery such as in endoscopic surgery and in particular in ultrasonic-assisted liposuction. These tools include a skin protector, properly speaking, and accessories consisting of an introducer member and a driver member. The skin protector thereby protects the skin in the area of the incision from both thermal and frictional abrasion and, according to an important feature of the invention, can be reliably anchored in the incision to minimize the likelihood of inadvertent removal or withdrawal of the skin protector out of the incision. As an additional optional feature, the skin protector may also be provided with an additional vacuum connection to decrease the amount of time required for removal of aspirate and to keep the surgical procedure as neat as possible. This may be achieved by providing an additional source of vacuum at the incisional site which is connected to the skin protector. The additional source of vacuum serves a double purpose. On the one hand, it increases the amount of aspirate which can be removed and, on the other, it increases the neatness of the procedure by minimizing the effect of leakage of any emulsion or other fluid substances that occur between the canula and the interior of the skin protector. A previous proposal to insert an annular seal about the probe to reduce this problem entailed the disadvantage of significantly reducing the degree of freedom of motion of the probe by the physician which is necessary for an efficient and successful procedure.

In one embodiment, the skin protector is provided with a lower part, adjoined by a flange-like part intended to rest on the outer surface of the skin, which may be followed by an upper part. In another embodiment, the upper part may be merged with the flange-like part so that the upper part itself then forms directly the flange-like part. In still another embodiment, the upper part may be omitted altogether and in still a further embodiment, the upper part merged with the flange-like part, may be considerably reduced in axial length. The optional feature of the additional vacuum connection may be incorporated into the thus-combined upper and flange-like part. The additional vacuum connection may be of any conventional construction. For example, the upper part or flange-like part may be provided with a connecting part or a stub-like connecting portion for the connection of a connecting nipple. A swivel joint may also be used to enable connection with a suction line that is freely rotatable relative to the skin of the patient. However, to avoid injury to the skin within the area of the incision the lower part of the skin protector according to this invention, which is intended to be implanted into the incision, should be provided with some anchoring means to minimize the likelihood of inadvertent removal or withdrawal of the skin protector out of the incision which might have undesirable consequences.

The skin protector and accessories of this invention made by conventional injection-molding techniques include a skin protector, preferably a one-piece skin protector and preferably made from gas (ETO) or steam sterilizable material which resists deformation and incorporates an outer configuration to aid in maintaining positioning in situ during the operative procedure; the introducer member serves for blunt dissection of a tunnel to allow insertion of the skin protector and ultrasonic probe and to serve also as a guide in the creation of an appropriate sized skin incision, when applicable, and the driver member serves for dilatation of the skin incision and for insertion and removal of the skin protector. Because the probe is continuously placed in motion by the surgeon during the procedure, not only in a direction perpendicular to the incision but is also moved laterally in directions covering as much as 360°, it is important that the skin protector be securely fastened in the incision to assure maintaining positioning in situ. In a preferred embodiment, this is attained by a rib-like anchoring spiral along the lower part of the skin protector as will be described more fully hereinafter. However, the fastening of the skin protector may also be achieved by any other anchoring means such as a threaded configuration, barbs, textured surfaces, ribs extending in circumferential direction or in more or less axial directions or any other known means. However, several threaded or spiral configurations are preferred as they allow for less trauma to the skin upon insertion and during in-vivo use.

U.S. Pat. No. 5,213,567 to Masaki discloses a skin-protecting device for preventing abrasive injury in the use of fat-aspirating devices. However, the skin-protecting device of this patent cannot be securely anchored to maintain positioning in situ which is a significant drawback with the requirement of a continuous motion of the probe or canula by the surgeon.

BRIEF DESCRIPTION OF THE DRAWINGS

These and other objections, features and advantages of the present invention will become more apparent from the following description when taken in connection with the accompanying drawing which shows, for purposes of illustration only, several embodiments of this invention, and wherein:

FIG. 3A is an elevational view of an introducer member for use with the skin protector of this invention;

FIG. 3B is an elevational view of a driver member for use with the skin protector of this invention, also showing the skin protector body and nipple disassembled from one another;

FIG. 3C is an elevational view, partly in cross section, illustrating the assembled skin protector and nipple with the installed driver member;

FIG. 8 is an elevational view of a modified embodiment of a driver member for use with the skin protector of FIG. 6;

FIG. 9 is a plan view on the driver member of FIG. 8;

FIG. 10 is an elevational view of another modified embodiment of a skin protector, similar to FIG. 6, in which the additional vacuum connection is incorporated into the flange-like part; and FIG. 11 is a plane view on the skin protector of FIG. 10.

DETAILED DESCRIPTION OF THE DRAWINGS

Figure 1:
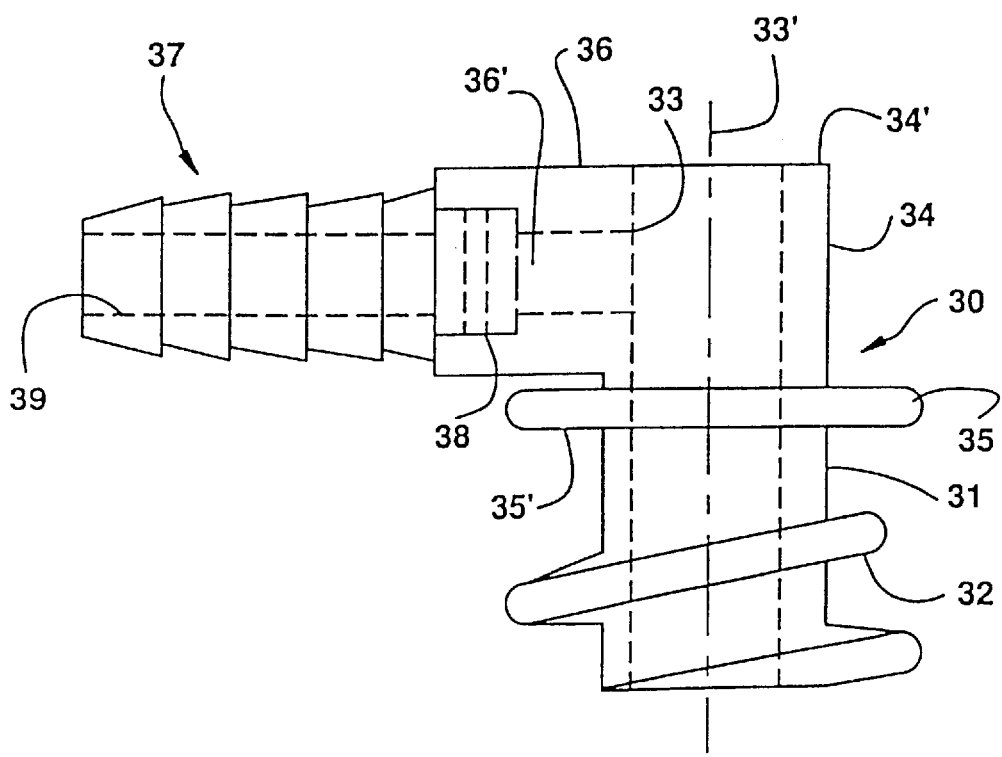
FIG. 1 is an elevational view of one embodiment of a skin protector of this invention, on an enlarged scale.

Referring now to the drawing wherein like reference numerals are used throughout the various views to designate like parts, the skin protector generally designated by reference numeral 30 (FIGS. 1, 2A and 2B) includes a lower part 31 of tubular configuration, preferably of cylindrical configuration which, in the embodiment of FIG. 1, is spaced from the upper part 34 by a flange-like annular part 35 of larger diametric dimension, for example, in the form of an annular disk whose lower surface 35' forms an abutment surface and is intended to rest on the external surface of the skin. A through-bore 33 extending through the upper part 34, the flange-like part 35 and the lower part 31 defines an axial direction 33'. As the cross-sectional area of the flange-like part 35 at right angle to the axial direction 33' is larger than the cross-sectional area of the lower part 31, also at right angle to the axial direction 33', the lower surface 35' of the flange-like part 35 which is intended to rest on the outer surface of the skin, limits at the same time the insertion depth of the skin protector into the incision. In order to anchor the lower part 31 in the incision and thereby reduce the likelihood of inadvertent removal of the skin protector during the surgical operation, the lower part 31 is provided with anchoring means which preferably includes a rib-like spiral 32 extending about the outer surface of the lower part 31. The rib-like spiral 32 thereby extends upwardly from the lower free end of the lower part 31 to a point spaced about 4 mm. from the lower surface 35' of the flange-like part 35, i.e., a distance corresponding approximately to the thickness of the skin consisting of epidermis and dermis so that the rib-like spiral 32 will be located in the area of the subcutaneous tissue. However, the anchoring means may also be of any other known construction, for example may be formed by a textured outer surface of the lower part, by one or more annular rib-like parts extending about the outer surface of the lower part with the distance of the annular rib-like part closest to the lower surface 35' amounting again to about 4 mm., or by non-spirally shaped ribs extending in the more or less axial direction which may be tapered and reach a maximum height in the radial direction about 4 mm. from the lower surface 35'. The free end of the lower part 31 may also be provided with a barb of small dimension whose outer surface increases in the direction toward the surface 35'.

The additional vacuum connection, which in the embodiment of FIG. 1 is located in the upper part 34, may be of any conventional construction. In one embodiment, it may include a nipple generally designated by reference numeral 37 which is provided with an internal bore 39 in communication with the internal bore 36' of the stub-like connecting portion 36 forming part of and integral with the upper part 34. The nipple 37, which is provided externally with conventional barbs, is connected with the stub-like connecting portion 36 in any known manner, for example, by way of a conventional swivel joint 38 so as to permit the suction line (not shown), which provides the additional source of vacuum and which may rest on the skin of the patient, to freely rotate through 360° relative to the skin protector.

The upper part 34 and/or the flange-like part 35 may also have any other shape, such as a polygonal shape to facilitate insertion and removal of the skin protector by rotation thereof by means of manual rotation or in particular with the assistance of a driver member of complementary shape to that of the upper part or flange-like part so as to be able to engage with the upper part 34 or the flange-like part 35 for rotation in unison. Furthermore, the upper part 34 may also be made of such size and configuration that its cross-sectional area approaches that of the flange-like part 35 so that the flange-like part 35 merges into the upper part 34 and the lower end surface of the upper part adjoining the lower part 31 would then form directly the lower surface 35' (FIGS. 4, 6, 7, 10 and 11).

The angle defined by the axis of the bores 39 and 36' need not be at right angle but may also be at an angle different therefrom. Furthermore, in order to enhance the aspiration efficiency of the suction line, a seal in the form of an annular ring may be provided near the upper end of bore 33 within an annular groove provided thereat. By locating such a seal near the upper end of bore 33 and by choosing the flexibility of the material of the annular ring as well as its dimensions, it may be possible to obtain a viable compromise between desirability of free movement of the probe and efficiency of the aspiration.

Figure 2A:
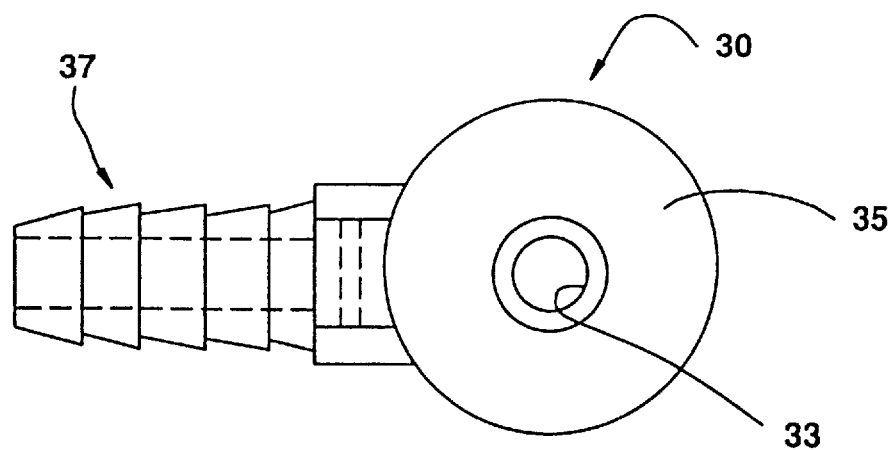
FIG. 2A is a plan view on the skin protector of FIG. 1, taken from below.
Figure 2B:
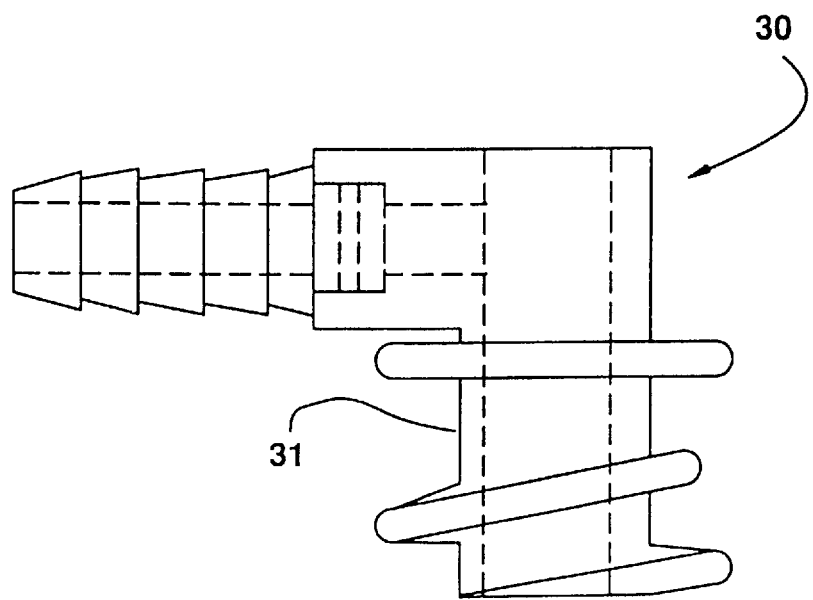
FIG. 2B is an elevational view on the skin protector of FIG. 2A.
Figure 4:
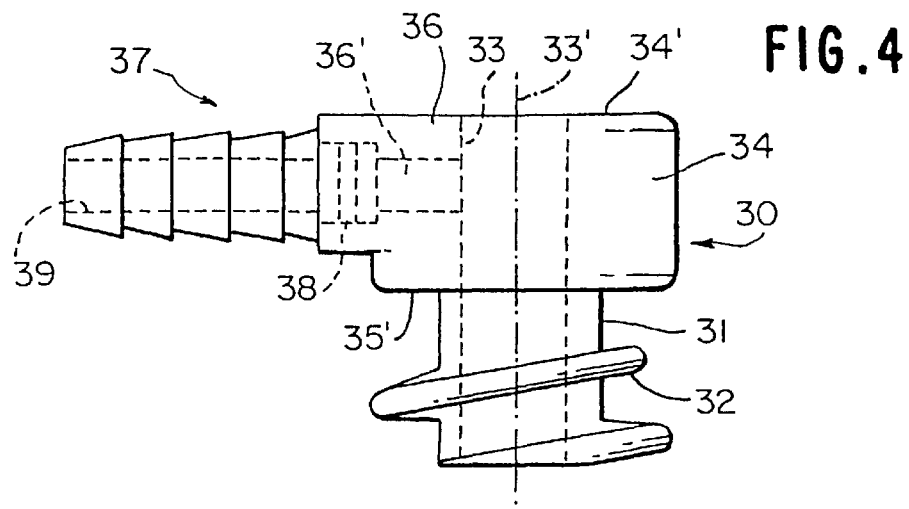
FIG. 4 is an elevational view of a modified embodiment of a skin protector according to this invention in which the upper part forms with its lower end surface the abutment surface resting on the outer surface of the skin.

FIG. 4 illustrates a skin protector 30 similar to FIGS. 2A and 2B in which the upper part 34 and the flange-like part are merged so that the upper part then forms directly the abutment surface 35'.

Figure 5:
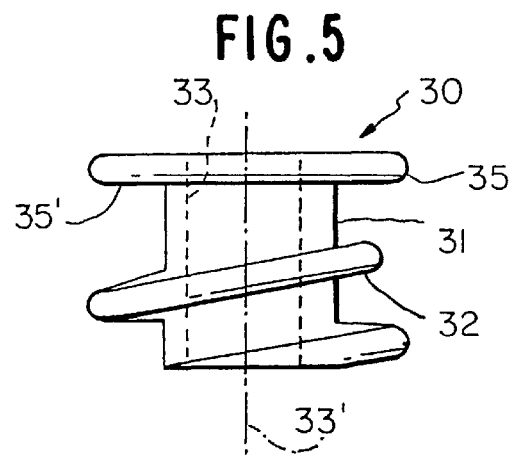
FIG. 5 is an elevational view of a still further modified embodiment of a skin protector according to this invention in which the upper part is omitted altogether to leave only a flange-like part.

FIG. 5 illustrates a skin protector 30 in which the upper part 34 together with the optional feature of the additional aspiration connection is omitted so that only the flange-like part 35 of the upper part 34 of FIG. 4 remains. The flange-like part 35 of FIG. 5 may again be of annular shape though it may also be of any other shape, such as polygonal shape, to facilitate insertion and removal of the skin protector by rotary motion, in particular with the use of a driver member having a socket-like configuration of complementary shape. The embodiment of FIG. 5 does not offer the neatness attainable in the surgical procedure with the use of the additional aspiration of FIGS. 1 and 4, owing to leakage of emulsion and other fluid substances through the space between the outer surface of the probe and the internal surface of bore 33. However, the modified skin protector of FIG. 5, even without this additional aspiration feature, is very important as regards avoidance of injuries in such surgical procedure because it assures reliable protection of the skin in the area of the incision against injury due to thermal and frictional abrasion by means of a skin protector that can be securely fastened to maintain positioning in situ during the continuous motions imparted to the probe by the surgeon.

Turning now to FIG. 3A, this figure illustrates an introducer member generally designated by reference numeral 40 which includes a lower part 41 provided with a blunt end 42 and an upper handle part 43. The lower part 41 intended to be inserted into the incision to create a tunnel for the insertion of the skin protector has a diametric dimension larger than the bore 33 in the skin protector, preferably larger than the diametric dimensions of the lower part 31. The blunt end 42 may be of hemispherical shape.

FIG. 3B illustrates a driver member generally designated by reference numeral 50 for use with the skin protector of FIGS. 1, 2A and 2B which includes an upper handle part 51 and a lower introducer part 52. The driver member is thereby of such a construction as to facilitate the implantation and removal of the skin protector by rotary motion. In the embodiment of the skin protector of FIG. 1, the driver member 50 is provided with an axially extending cut-out 53 (FIG. 3B) in order to be able to mount the driver member 50 over the stub-like connecting portion 36 of the skin protector until its lower surface 53' abuts at the upper surface 34' of the upper part 34. This cut-out 53 thereby extends in the axial direction and is of such dimension as to accommodate the stub-like connecting portion 36. Moreover, this cut-out 53 is not just an axial cut-out but is provided with a further cut 53' so that when the driver member 50, installed over the skin protector 30, is rotated in the counterclockwise direction, a C-shaped lip is formed whose lower end then extends below the stub-like connecting portion 36 in order to be able to withdraw the skin protector together with the driver member 50 in the axial direction, i.e., in a direction opposite to the direction of the rib-like spiral 32. When rotating the driver member in the clockwise direction, the rib-like spiral then assists in implanting the skin protector into the incision.

In connection with the skin protector of FIG. 5, which consists of a lower part 31 with a spiral anchoring means 32 and of a flange-like part 35, the driver member is again constructed to accommodate the physical dimensions of the skin protector. For example, if the flange-like part 35 of the skin protector of FIG. 5 is of polygonal shape, the driver member may be in the form of a socket wrench with which to engage the polygonal outer surface of the skin protector. Conversely, the flange-like part 35 of FIG. 5 may be of annular shape and may be provided with a polygonal recess in the upper exposed surface in which case the driver member may be constructed of complementary polygonal shape to engage in the polygonal recess. Furthermore, any complementary configurations in the lower end of the driver member and the upper surface of the skin protector, which permit a mechanical coupling, as known to those skilled in the art, may be used.

Typical dimensions of one embodiment of the skin protector of FIG. 1, of the introducer member of FIG. 3A and of the driver member of FIG. 3B are as follows, the values being in appropriate units, such as millimeters. The overall axial height of the skin protector is 20.3 mm.; the axial height of the lower part 31 is 10 mm.; the diameter of the through-bore 33 is 5.5 mm.; the diameter of the internal bore 39 is 3.0 mm.; the height of the rib-like spiral 32 from the lower part 31 is 3.2 mm.; and the overall length of the nipple 37 to the opposite side of the upper part 34 is 27.5 mm. The overall length of the introducer member 40 is 130.8 mm., and the diameter of the lower part 41 is 8.1 mm. The overall length of the driver member 50 is 102.6 mm., and the diameter of the lower introducer part 52 is 5.4 mm. However, it is understood that these dimensions are merely for purposes of illustration and are not to be considered limitative of the invention as they may be modified as known to those skilled in the art. The body of the skin protector 10, which is made in one piece of plastic material by conventional techniques, is preferably made from gas (ETO) or steam sterilizable material which resists deformation and incorporates an outer configuration to aid in maintaining positioning in situ during the operative procedure.

Figure 6:
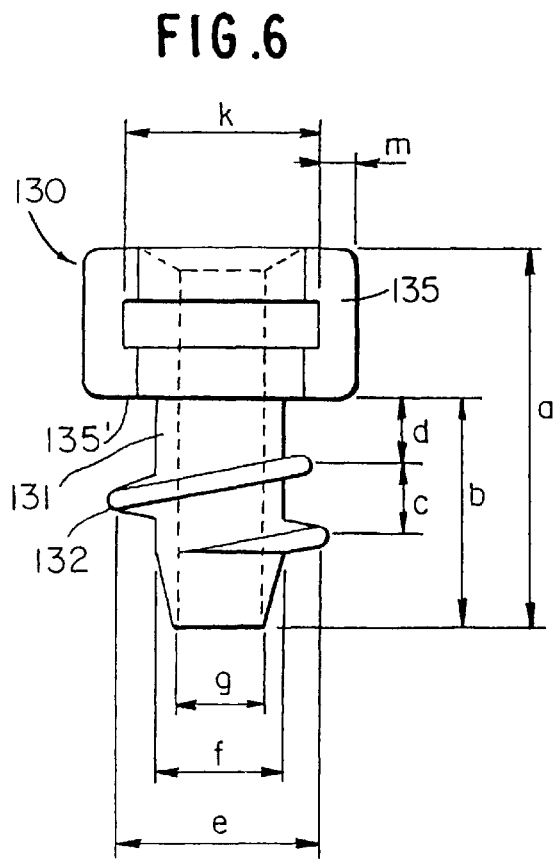
FIG. 6 is an elevational view of a still further modified embodiment of a skin protector of this invention.
Figure 7:
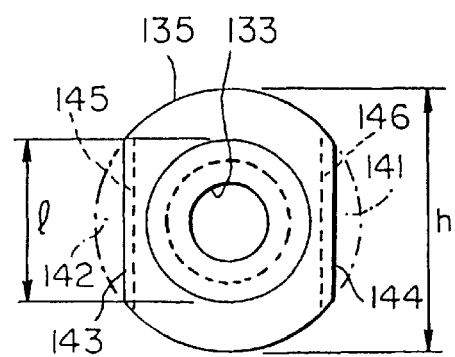
FIG. 7 is a plan view on the skin protector of FIG. 6.

In the embodiment of FIGS. 6 and 7, parts of the skin protector corresponding to those of the skin protector of FIGS. 1, 4 and 5 are designated by corresponding reference numerals of the 100 series. The skin protector generally designated by reference numeral 130 again includes a lower part 131 provided with some anchoring means, preferably a rib-like spiral 132 and an annular flange 135 with which a reduced upper housing is combined and which again forms an abutment surface 135'. At its exposed upper end, the annular flange-like part 135 includes set-back surfaces 141 and 142 of segmental-like shape forming rectilinear axial surfaces 143 and 144 which extend parallel to one another. Each of the surfaces 143 and 144 are also undercut at 145 and 146 (FIG. 7) for engagement with corresponding parts of the driver member as will be explained.

The driver member (FIGS. 8 and 9) whose handle section now consists of a number of annular parts 151*a*, 151*b*, 151*c* and 151d interconnected as shown in FIG. 8, includes a head portion 153 provided with a central transversely extending slot 154 whose parallelly axial wall surfaces 154a and 154b are spaced from each other by a distance substantially equal to or slightly larger than the transverse spacing of undercuts 145 and 146 (FIG. 7). Additionally, the walls 154a and 154b forming slot 154 are undercut at 155 and 156 to accommodate the lips formed by undercuts 145 and 146 to permit the driver member to be installed over the raised part of the skin protector formed by surfaces 143 and 144 by sliding movement in the direction of slot 154. By rotation in either direction of the handle section 151, the skin protector is taken along and caused to rotate for implantation and withdrawal thereof. The dash-and-dot line circles in FIG. 9 indicate the cutters used to mill out the undercuts 155 and 156 of FIG. 8.

Typical dimensions of one embodiment of the skin protector and of the driver member illustrated in FIGS. 6–9, indicated herein only as illustrative but non-limitative of the present invention are as follows, the values being in appropriate units such as inches. The length a of the skin protector of FIG. 6 is 0.984 inches; the overall length b of the lower part 131 is 0.591 inches; the pitch of the spiral rib-like anchoring means c is 0.179 inches; and the spacing d between the surface 135' and the end of the rib-like anchoring means 132 is 0.171 inches. The maximum diameter e of the spiral rib-like anchoring means is 0.521 inches; the outside diameter f of the lower part 131 is 0.325 inches and the minimum diameter g of the tapering end of the lower part is 0.236 inches. The overall diameter h of the flange-like part 135 is 0.703 inches; the spacing k of the undercut is 0.503 inches and the dimension 1 (FIG. 7) is 0.433 inches. The spacing m from the outer surface of the flange-like part 135 to the undercut is 0.081 inches. The diameter of the through-bore is 0.212 inches while the countersunk is formed by a surface 120° and 0.125 inches in depth.

The driver member 150 includes four handle sections 151a through 151d of a diametric dimension of 0.87 inches while the lower section 152 has a diametric dimension of 0.177 inches. The overall length p of the handle section is 3.2 inches; and the overall length q of the lower section 152 is 1.15 inches. However, it is understood that these dimensions may be varied as known to those skilled in the art.

The embodiment of the skin protector of FIGS. 10 and 11 differs from that of FIGS. 6 and 7 only in that the flange-like part 135 is provided with an optional vacuum connection of any conventional construction and generally designated by reference numeral 160 which is connected by way of a cross-bore 161 with the through-bore 133. A typical value indicated herein only for illustrative but non-limitative purposes of the diameter of the connecting channel 161 is 0.157 inches while the internal bore 162 of the connection has a diameter of 0.217 inches and is provided with an internal thread for a threaded connection with a nipple adapted to be connected with a vacuum line. As to the rest, the embodiment of FIGS. 10 and 11 is similar to that of the embodiment of FIGS. 6 and 7.

During surgical liposuction procedure, a skin protector is positioned through the skin incision prior to insertion of the probe. The probe is then inserted through the port of entry in the skin protector formed by the through-bore, thus eliminating direct contact between the probe and the incisional site. The port of entry may also be larger like a funnel, cup etc., to increase the target area of the port of entry to further aid in the prevention of the probe or canula coming in contact with the skin. The larger surface area or external diameter provides additional material for protection against direct contact between the probe and the skin by such funnel-shaped devices. Of course, the skin protector of this invention can also be used with similar advantages with liposuction without ultrasonic-assist. In fact, it is currently used during the so-called clean-up operation of the surgical procedure with the use of only ordinary probes without ultrasonic-assist after completing the procedure with the use of an ultrasonic-assisted probe. Moreover, the skin protector of this invention may also be applied to endoscopic surgery or other procedures which require a need for protecting the incisional site from frictional or thermal abrasion.

The skin protector of this invention can be made small in physical dimensions to advantageously minimize the required length of the incision, and to allow for implantation and use thereof in areas with smaller probes, also in areas of less subcutaneous tissue volume. The outlet for the optional additional vacuum connection may include an integrated locking swivel joint to permit full rotation of the vacuum line during the surgical procedure, yet prevents passive disconnection of the additional vacuum source. The vacuum line may be connected to a standard operating room supply and suction reservoir or to a portable vacuum source. The barbed outer surface of the nipple is provided to accommodate most standard-sized suction tubing.

Examples of materials demonstrating characteristics of durability include, for example, ultra high molecular weight polyethylene (UHMWPE) (DELRIN®) and ULTEM®. Parts made of ULTEM® permit standard steam autoclave procedures where desired. Both of these materials resist fragmentation and particulation with direct transverse contact of the ultrasonic probe. However, other materials offering similar characteristics may also be used, including those used for throw-away medical parts. The skin protector is inserted into the skin incision with the aid of the driver turning the driver member in a clockwise direction and thereby anchoring the skin protector in the subcutaneous tissues by means of the rib-like anchoring spiral. The skin protector may then be removed again by using the driver to turn in a counterclockwise direction.

As mentioned above, the outer configuration of the skin protector may also include various anchoring configurations for maintaining temporary implantation in situ, whereby the anchoring configuration is placed at a distance to the base or abutment surface of the skin protector in order to decrease undue stress on the skin at the incisional site.

While we have shown and described several embodiments of a skin protector in accordance with this invention, it is understood that the same is not limited thereto but is susceptible of numerous changes and modifications as known to those skilled in the art. For example, in lieu of a symmetrical shape (e.g. circular), the skin protector may also be of asymmetrical shape, such as oval shape, if probe movements in one or two directions are to be favored. Furthermore as mentioned above, any other means may be provided along the outer surface of flange-like part 35 to facilitate manual rotation thereof by the surgeon, such as knurled surfaces or otherwise roughened surfaces. We therefore do not wish to be limited to the details shown and described herein but intend to cover all such changes and modifications as are encompassed by the scope of the appended claims.

We claim:

1. A skin protector for protecting the skin incision from thermal and frictional abrasion caused by movements of a probe adapted and intended to move freely and continuously inside the skin protector during a surgical procedure, comprising a skin protector body made of ultrasonic-compatible material including first means forming a lower part for insertion into the incision to access the subcutaneous space and second means in one piece with said first means and intended to remain external of the skin, said second means providing limiting means for limiting the insertion depth of the first means of the skin protector in the subcutaneous space, said body being provided with a substantially aligned bore defining an axial direction and of a diametric dimension allowing free movement of a probe inside said skin protector during the surgical procedure, and further means directly on and integral with the outer surfaces of the lower part to enable anchoring of said skin protector body in the incision and thereby maintain the in-situ position of the skin protector by lessening the likelihood of unintentional withdrawal of the skin protector out of the incision during movements of the probe.

2. A skin protector according to claim 1, wherein said limiting means includes abutment surface means intended to face the skin externally and having a cross-sectional area larger than the cross-sectional area through said lower part at a substantially right angle to the axial direction.

3. A skin protector according to claim 2, wherein said second means has a lower end surface, and wherein said abutment surface means is formed directly by said lower end surface.

4. A skin protector according to claim 2, wherein said abutment surface means is formed by an annular disk-like part.

5. A skin protector according to claim 1, wherein said anchoring means is formed by one of rib-like means, a textured outer surface of the lower part, barb means and threaded means.

6. A skin protector according to claim 5, wherein said lower part has an outer surface and a free end, and wherein said anchoring means is formed by at least one rib-like means provided over at least a portion of the outer surface of the lower part.

7. A skin protector according to claim 6, wherein said rib-like means is spaced from said limiting means by a distance corresponding approximately to the thickness of the skin consisting of the epidermis and dermis.

8. A skin protector according to claim 7, wherein said rib-like means is spirally shaped commencing in the area of the free end of the lower part and extends spirally upwardly about said lower part in the direction toward the limiting means.

9. A skin protector according to claim 8, wherein said spirally shaped rib-like means terminates at a distance from said limiting means corresponding approximately to the thickness of the skin consisting of epidermis and dermis.

10. A skin protector according to claim 1, wherein said lower part is of cylindrical shape.

11. A skin protector according to claim 1, wherein said second means includes means to facilitate implantation of the skin protector into the incision by rotary motion.

12. A skin protector according to claim 11, wherein said means to facilitate implantation is formed by a non-circular shape of the second means.

13. A skin protector according to claim 11, wherein said means to facilitate implantation is formed by non-smooth external surfaces of said second means.

14. A skin protector according to claim 11, wherein said means to facilitate implantation includes a driving member, and wherein said skin protector and driving member include coupling means to cause said skin protector to rotate in unison with rotation of said driving member.

15. A skin protector according to claim 14, wherein said coupling means is a mechanical coupling means.

16. A skin protector according to claim 14, wherein said coupling means is formed by complementary configurations.

17. A skin protector according to claim 1, wherein said skin protector body includes vacuum-assisted means to remove at least a large part of the emulsion and other fluid substances seeking to leak out through the space between a probe and the through-bore.

18. A skin protector according to claim 1, wherein said second means is formed at least in part by a disk-like member.

19. A skin protector according to claim 18, further comprising vacuum-assisted means incorporated into said disk-like member to remove at least a large part of the emulsion and other fluid substances seeking to leak out through the space between a probe and the through-bore.

20. A skin protector according to claim 18, wherein said disk-like member is of non-circular shape.

21. A skin protector according to claim 1, wherein said anchoring means terminates at a distance from said limiting means corresponding approximately to the thickness of the skin consisting of epidermis and dermis.

* * * * *